United States Patent [19]

Massie

[11] 3,992,423

[45] Nov. 16, 1976

[54] PRODUCTION OF CARBOXYLIC ACIDS FROM OLEFINS WITH A ZEOLITE IN ALUMINUM HYDROSOL CATALYSTS

[75] Inventor: Stephen N. Massie, Palatine, Ill.

[73] Assignee: Universal Oil Products Company, Des Plaines, Ill.

[22] Filed: Dec. 26, 1974

[21] Appl. No.: 536,537

[52] U.S. Cl. ............... 260/410.6; 260/410.9 R; 260/413; 260/468 M; 260/486 AC; 260/497 C; 260/514 M; 260/533 A
[51] Int. Cl.[2] ............... C07C 67/38; C07C 51/14; C07C 69/24; C07C 69/74
[58] Field of Search .......... 260/413, 410.9 R, 410.6, 260/410, 533 A, 514 M, 468 M, 497 R, 486 AC, 497 C; 252/455 Z

[56] References Cited
UNITED STATES PATENTS

| | | | |
|---|---|---|---|
| 1,973,662 | 9/1934 | Schalch | 260/533 A |
| 3,346,625 | 10/1967 | Fenton et al. | 260/413 |
| 3,397,226 | 8/1968 | Fenton | 260/468 M |
| 3,677,973 | 7/1972 | Mitsche et al. | 252/455 Z |
| 3,798,177 | 3/1974 | Reed et al. | 252/455 Z |
| 3,880,938 | 4/1975 | Massie | 252/455 Z |

Primary Examiner—Winston A. Douglas
Assistant Examiner—P. E. Konopka
Attorney, Agent, or Firm—James R. Hoatson, Jr.; Raymond H. Nelson; William H. Page, II

[57] ABSTRACT

Carboxylic acids are prepared by a process which comprises the treatment of an unsaturated hydrocarbon with a compound containing a hydroxy group and carbon monoxide in the presence of a catalyst comprising a zeolite which has been treated by dispersing said zeolite in an alumina hydrosol prior to aging and subsequently drying.

15 Claims, No Drawings

PRODUCTION OF CARBOXYLIC ACIDS FROM OLEFINS WITH A ZEOLITE IN ALUMINUM HYDROSOL CATALYSTS

This invention relates to an improvement in a process for the production of carboxylic acids. More specifically, this invention relates to a process for the preparation of a carboxylic acid which comprises the treatment of an unsaturated hydrocarbon with a compound containing a hydroxy group and carbon monoxide in the presence of a catalyst comprising a zeolite which has been treated by dispersing said zeolite in an alumina hydrosol prior to aging and subsequently drying.

Processes directed to the production of carboxylic acids are well known in the art of chemistry. One such process comprises the production of monocarboxylic acids from straight-chain or branch-chain monoolefins by the reaction of carbon monoxide in a stoichiometric amount of water with an aliphatic or cycloaliphatic monoolefin in the presence of a catalyst comprising a mineral acid. This process is commonly known as the Koch reaction and may be exemplified by the reaction of 1-pentene to its corresponding carboxylic acid in the presence of a catalyst comprising hydrogen fluoride. It has also been shown in the prior art that straight or branched-chain aliphatic or alicyclic olefins having up to 24 carbon atoms may be carboxylated by the treatment with carbon monoxide and water, the reaction being effected by the gradual addition of said olefins to the reaction system containing a substantial molar excess of mineral acid catalyst per mole of the olefin. The known molar ratio for optimum results has been shown to be between 10 to 20 moles of hydrogen fluoride per mole of olefin as exemplified by U.S. Pat. No. 3,661,951. It should be noted that the process of the present invention possesses the substantial advantage of not necessarily having to adjust molar ratios to obtain optimum results. It is also known in the prior art that the dispersing of a zeolite in an alumina hydrosol, prior to forming by methods known in the art of catalyst preparation, will further enhance the activity and life of the catalyst. One of the catalytic reactions which is known in the prior art is a cyclialkylation of a primary amine with an oxygenated heterocyclic compound.

In contradistinction to the prior art it has now been discovered that a carboxylic acid may be prepared by the treatment of an unsaturated hydrocarbon with a compound containing a hydroxy group and carbon monoxide in the presence of a catalyst comprising a zeolite which has been treated by dispersing said zeolite in an alumina hydrosol prior to aging and drying. Utilization of the present invention will create an increase in speed and percentage conversion of reactants which will reduce the manufacturing time and cost of the final product to the manufacturer and to the consumer. Utilization of the present invention will also result in the allowance of the preparation of the carboxylic acids from the unsaturated hydrocarbons in a manner of decreased pressures and temperatures, thereby conserving energy in the preparation of the desired products.

The desired products of this invention, namely, carboxylic acids, are utilized in the chemical industry in many ways. For example, carboxylic acids are used in the rubber industry as antiseptics; as fungicides; in perfumes; as tanning agents; as deliming agents; for the preparation of butter; and the preparation of certain pharmaceuticals; in water purification; as emulsifying agents; as sweetening agents for gasoline. For example, nonanoic acid may be utilized as a lacquer; as a plastic; in hydrotropic salt production; in the synthesis of flavors and odors; and as a vinyl plasticizer. It should also be noted that derivatives of carboxylic acids, namely, esters of the carboxylic acids may also be included within the definition hereinafter set forth for the resultant carboxylic acid product. The derivatives or esters of the carboxylic acid may be utilized as soaps or animal foods as a result of subsequent sulfation or ethoxylation to form various surfactants.

It is therefore an object of this invention to provide a process for the preparation of carboxylic acids.

A further object of this invention is to provide a process for the preparation of carboxylic acids utilizing certain catalytic compositions of matter which will permit the production and recovery of the desired carboxylic acids in a more pecuniarily rewarding manner.

In one aspect an embodiment of this invention resides in a process for the production of carboxylic acids which comprises the treatment of an unsaturated hydrocarbon with a compound containing a hydroxy group and carbon monoxide at reaction conditions in the presence of a catalyst comprising a zeolite which has been treated by dispersing said zeolite in an alumina hydrosol prior to aging at aging conditions, drying at drying conditions, and recovering the resultant carboxylic acid.

A specific embodiment of this invention resides in a process for preparing a carboxylic acid which comprises the treatment of 7-tetradecene with carbon monoxide and a quantity of water equal to or in excess of the stoichiometric quantity required for the unsaturated compound in the presence of a catalyst which comprises mordenite which has been dispersed in an alumina chloride hydrosol, aged at a temperature of from about 50° to about 250° C. and a pressure of 1 atmosphere and dried at a temperature of 100° to about 500° C. and a pressure of 1 atmosphere for a period of time comprising 5 hours, said treatment of the unsaturated compound being performed at a temperature from about 25° to about 300° C. and 100 atmospheres of carbon monoxide pressure and recovering the resultant carboxylic acid, namely pentadecanoic acid.

A second specific embodiment of this invention resides in a process for preparing a carboxylic acid which comprises the treatment of 2-nonene at reaction conditions which include a temperature of 200° C. and a pressure of 200 atmospheres of carbon monoxide-inert gas pressure in the presence of a zeolitic material comprising faujasite which has been dispersed in an alumina hydrosol comprising 67% aluminum chloride and 33% aluminum sulfate, aged at a temperature of 250° C. at a pressure of 1 atmosphere for a period of 10 hours and dried at 500° C. and a pressure of 1 atmosphere, and recovering the resultant decanoic acid.

Other objects and embodiments will be found in the following further detailed description of the present invention.

As hereinbefore set forth, the present invention is concerned with a process for preparing carboxylic acids which comprises the treatment of an unsaturated hydrocarbon with a compound containing a hydroxy group and carbon monoxide in the presence of a catalyst comprising a zeolite which has been treated by dispersing said zeolite in an alumina hydrosol prior to aging and drying. The reaction is effected under reaction conditions which include a temperature in the range of from about 25° C. to about 300° C. and a pressure of from about atmospheric to about 500 atmospheres or more. In addition, the zeolite which has been treated by dispersal in an alumina hydrosol may be aged at aging conditions and dried at drying conditions. The aging conditions of the present invention include a temperature of from about 30° to about 500° C. and a pressure in the range of from about 1 to about 100 atmospheres for a period of time comprising from about 1 to about 20 hours. The drying conditions of the present invention include a temperature of from about 100° to about 500° C. and a pressure of from about 1 atmosphere to about 100 atmospheres. The superatmospheric pressures of the reaction conditions may be afforded by the introduction of carbon monoxide gas to the reaction system for a period of time to enable the pressure in the reaction vessel or reaction zone to stabilize, or the pressure may be afforded partially by the carbon monoxide gas and partially by any inert gas such as nitrogen or helium to increase the pressure in the reaction vessel or reaction zone to the desirable level. The superatmospheric pressures contemplated in the aging or drying conditions may be afforded by the introduction of any substantially inert gas such as nitrogen or helium. In a preferred embodiment of this invention, it is contemplated that the molar ratio of the reactants may be present in such a range that the hydroxy group is present in a predetermined stoichiometric excess in comparison to the unsaturated hydrocarbon. The stoichiometric excess may be of great magnitude or it may be of slight excess, the slight excess of the stoichiometric amount being preferred as most economically feasible.

The molar ratio or quantity of the zeolitic catalyst which has been treated by dispersing said zeolite in an alumina hydrosol prior to aging and drying may also vary widely. In order to insure a sufficiently high rate of carboxylic acid production, it is contemplated within the scope of the present invention that the zeolitic material be present in a molar excess of about 10 moles of zeolitic material to every mole of the unsaturated hydrocarbon compound. The minimum quantity of zeolitic molar material would cmprise less than the molar amount of the unsaturated hydrocarbon but enough to effect the reaction economically.

Examples of suitable mixtures of unsaturated hydrocarbons or unsaturated hydrocarbons by themselves which are utilized as a starting material in the process of the present invention would include, in particular, all aliphatic olefinic compounds possessing from about 2 to about 20 carbon atoms, aliphatic alkyl-substituted olefinic compounds possessing from about 4 carbon atoms to about 32 carbon atoms, cycloolefinic compounds possessing from about 5 to about 10 carbon atoms or alkyl-substituted cycloolefinic compounds possessing from about 5 carbon atoms to about 32 carbon atoms such as 1-butene, 2-butene, isobutylene, 1-pentene, 2-pentene, 2-methyl-1pentene, 2-methyl-2-pentene, 1-heptene, 2-heptene, 3-heptene, 2-methyl-2-hexene, 3-methyl-2-hexene, 1-octene, 2-octene, 3-octene, 4-octene, 3-methyl-1-heptene, 2-methyl-2-heptene, 1-nonene, 2-nonene, 3-nonene, 4-nonene, 3-methyl-2-octene, 1-decene, 2-decene, 3-decene, 4-decene, 5-decene, 3,4-dimethyl-3-octene, 4-ethyl-2-octene, 1-undecene, 2-undecene, 3-undecene, 4-undecene, 5-undecene, 1-dodecene, 2-dodecene, 3-dodecene, 4-dodecene, 5-dodecene, 6-dodecene, 1-tridecene, 2-tridecene, 3-tridecene, 4-tridecene, 5-tridecene, 6-tridecene, 1-tetradecene, 2-tetradecene, 4-tetradecene, 5-tetradecene, 6-tetradecene, 7-tetradecene, 1-pentadecene, 3-pentadecene, 5-pentadecene, 6-pentadecene, 7-pentadecene, 1-hexadecene, 3-hexadecene, 5-hexadecene, 7-hexadecene, 1-heptadecene, 2-heptadecene, 4-heptadecene, 6-heptadecene, 3-octadecene, 4-octadecene, 5-nonadecene, 1-nonadecene, cyclopentene, cyclohexene, cycloheptene, cyclooctene, cyclononene, cyclodecene, 4,5-diethyl-1-cyclopentene, 3,4,5,6-tetrabutyl-1-cyclohexene, 1,2,3-triamyl-1-cycloheptene, 2,3,4,5-tetra-n-amyl-1-cyclooctene, 3,4,5,6-tert-n-hexyl-1-cyclooctene, 3,5-di-n-butyl-1-cyclononene 3,4-diethyl-1-cyclodecene, etc.; or mixtures of internal and terminal olefins such as internal and terminal olefins possessing carbon numbers ranging from 6 to 7, 8 to 10, 11 to 14, 15 to 18 and 18 to 21. It is also contemplated within the scope of this invention that diolefins (alkadienes and cycloalkadienes) may be included within the term "unsaturated hydrocarbon compound," however, these compounds may give a result which is not necessarily equivalent to those of the monounsaturated hydrocarbon reactions. The diolefins may be exemplified by 1,4-nonadiene, 1,7-octadiene, 1,3-heptadiene, 1,2-heptadiene, 1,5-hexadiene, 1,3-pentadiene, 1,4-cyclohexadiene, 1,5-cyclooctadiene, etc. In general, nonconjugated diolefins are preferred over conjugated diolefins.

Suitable examples of compounds containing a hydroxy group would include water, ethylene glycol, propylene glycol, butylene glycol, pentylene glycol, hexylene glycol, heptylene glycol, octylene glycol, nonylene glycol, decylene glycol, methanol, ethanol, propanol, butanol, pentanol, hexanol, heptanol, octanol, nonanol, decanol, etc. It should be noted that when an organic alcohol or glycol is substituted for water in the definition of the compound containing a hydroxy group that the resultant carboxylic acid produced from the above-described reaction is a derivative of carboxylic acid, namely, a hydroxy alkyl ester, however, the definition of carboxylic acid used in the specification and appendant claims is herein defined to include all carboxylic acids and all hydroxy alkyl esters of carboxylic acids.

It is contemplated within the scope of this invention that the reaction may be effected in a medium which will comprise an inert organic compound. Suitable examples of inert organic mediums would comprise n-pentane, n-hexane, n-heptane, isooctane (2,2,4-trimethylpentane), benzene, toluene, pseudocumene, cyclopentane, cyclohexane, cycloheptane, etc. It is understood that the aforementioned unsaturated compounds, compounds containing a hydroxy group and inert organic mediums are only representative of the class compounds which may be employed, and that the present invention is not necessarily limited thereto.

The catalytic compositions of matter which are used in the process of this invention comprise zeolites including both mordenite and faujasite. Zeolites are crystalline aluminosilicates comprising cages or cavities interconnected by smaller pores or channels of definite size range characteristic of each zeolitic variety. Since the dimensions of the pores and channels are such as to accept molecules of certain dimension while rejecting those of larger dimensions the materials have come to be known as molecular sieves and are utilized in many ways by taking advantage of these properties.

The zeolites are generally described as a three-dimensional network of fundamental structural units consisting of silicon-centered $SiO_4$ and aluminum-centered $AlO_4$ tetrahedra interconnected by a mutual sharing of apical oxygen atoms to effect a chemical balance, each $AlO_4$ tetrahedra has a cation associated therewith, typically sodium. The $SiO_4$ and $AlO_4$ tetrahedra are arranged in a definite geometric pattern often visualized either in terms of chains, layers or polyhedra. The zeolites comprise well-defined intra-crystalline dimensions including intra-crystalline channels and pores whose narrowest cross section has essentially a uniform diameter. The various zeolites may be classified according to the geometric pattern of their framework with its attendant pore size, and by the $SiO_2:Al_2O_3$ mole ratio of their compositions.

One type of zeolitic catalyst contemplated within the scope of this invention is mordenite. Mordenite is highly siliceous in nature and characterized by a $SiO_2:Al_2O_3$ mole ratio of from about 6 to about 12 as manufactured or found in its natural state. The mordenite crystal structure comprises four and five-membered rings of $SiO_4$ and $AlO_4$ tetrahedra so arranged that the resulting crystal lattice comprises pores and channels running parallel along the crystal axis to give a tubular configuration. Mordenite is unique among zeolites since the channels or tubes do not intersect and access to the cages or cavities is in only one direction, thereby giving the zeolitic structure its two-dimension configuration.

Another type of zeolitic catalyst contemplated within the scope of this invention is faujasite. Faujasite is characterized by a $SiO_2:Al_2O_3$ ratio of about 2 to about 6 and by pore openings in the range of from about 6 to about 15 Angstroms. The fundamental structural units, $SiO_4$ and $AlO_4$ tetrahedra are joined to form four-membered and six-membered rings and the rings are so arranged that the resulting structure resembles a truncated octahedron with the four-membered ring forming six sides or faces thereof and the six-membered ring forming the remaining eight sides or faces. The resulting truncated octahedra are interconnected at the the hexagonal faces through a hexagonal prism formed by two of the six-membered rings of tetrahedra to form a crystal lattice comprising cavities or cages in open communication through channels, thereby giving the zeolitic structure its three-dimensional configuration. Other natural zeolites which may be utilized include analcite, chabazite, heulandite, natrolite, stilbite and thomsonite. It is also contemplated within the scope of the process of this invention that synthetic zeolitic catalyst may also be utilized. The synthetic zeolites would include all those varieties ranging from gelatinous to porous or sandlike.

It was found that treatment of the zeolitic catalyst prior to its formation into the desired structure will change the life and activity of the catalyst. The treatment of the zeolite is found to be a two-step process; first where the zeolite is dispersed within an alumina hydrosol and second where it is aged and dried at the hereinbefore set forth conditions of aging and drying. An alumina hydrosol may be prepared from compounds such as aluminum chloride, aluminum bromide, aluminum sulfate, aluminum alcoholate, etc., the aluminum chloride being the most generally employed. Suitable examples of alumina hydrosols would include aluminum halide hydrosols, such as aluminum chloride sols, aluminum bromide sols, and aluminum-chloro-sulfate hydrosol and aluminum acetate hydrosol.

The process of this invention may be effected in any suitable manner and may comprise either a batch or a continuous type operation. For example, when a batch type operation is employed, the reactants comprising the unsaturated hydrocarbon compound, the compound containing a hydroxy group and carbon monoxide are placed in an appropriate apparatus along with a mordenite-alumina or faujasite-alumina catalyst (which have previously been heated to an elevated temperature for a predetermined increment of time to effect aging and dried at drying conditions). If atmospheric pressure is to be employed, the reaction vessel is then heated to a predetermined operating temperature and maintained thereat for a period of time which may range from 0.5 hour to 50 hours or more at which time the heating is discontinued and the vessel is allowed to return to room temperature. The reaction mixture is then recovered, separated from the zeolitic catalyst and subjected to conventional means of purification and separation, said means including washing, drying, filtration, extraction, evaporation, fractional distillation, etc., whereby the desired carboxylic acid is recovered. Alternatively, if superatmospheric pressures are to be employed in the reaction, the reactants comprising the unsaturated compound and the compound containing a hydroxy group are charged to a pressure vessel such as a rotating autoclave which contains a mordenite-alumina or faujasite-alumina catalyst prepared as hereinbefore described. The autoclave is sealed and carbon monoxide is pressed in until the desired operating pressure is reached. It is also within the scope of this invention that another inlet may be used to allow entry of a substantially inert gas such as nitrogen to attain the desired operating pressure by the addition of the partial pressure of the carbon monoxide and the partial pressure of the substantially inert gas. The autoclave is then heated to a desired operating temperature and maintained thereat for a predetermined residence time. At the end of this time heating is discontinued, the autoclave is allowed to return to room temperature and the excess pressure is discharged. The autoclave is opened and the reaction mixture is then treated in a similar manner to that hereinbefore set forth whereby the desired carboxylic acids are separated and recovered.

It is also contemplated within the scope of this invention that the reaction process for obtaining the desired carboxylic acids may be effected in a continuous manner of operation. When such a type of operation is employed, the reactants comprising the unsaturated compound, compound containing a hydroxy group and carbon monoxide are continuously charged to a reaction zone containing a mordenite-alumina or faujasite-alumina catalyst prepared as hereinbefore described, said vessel being maintained at proper operating conditions of temperature and pressure. After completion of the desired residence time, the reactor effluent is continuously withdrawn and subjected to conventional means of separation whereby the desired carboxylic acid is recovered, while any unreacted starting material comprising carbon monoxide, unsaturated hydrocarbons or a compound containing a hydroxy group are recycled to the reaction zone to form a portion of the feedstock. Inasmuch as the catalytic composition of matter is solid in nature, various types of continuous operations may be utilized. One type of operation comprises the fixed bed method in which the catalyst is disposed as a fixed bed in the reaction zone and the reactants are passed over said fixed bed in either an upward or downward flow. Another type of operation which may be employed comprises a moving bed type operation in which the catalyst and the reactants are passed through the reaction zone either concurrently or countercurrently to each other, or the slurry type operation in which the catalyst is carried into the reaction zone as a slurry in either or both of the reactants.

As hereinbefore set forth in the body of the specification the term "carboxylic acids" may be defined to include all carboxylic acids and all derivatives of carboxylic acids comprising hydroxy alkyl esters of the carboxylic acids. The hydroxy alkyl esters of the carboxylic acids are recovered when the compound containing a hydroxy group is selected from an alkanol, an alkyl glycol or any other alkyl compound containing polyhydroxy groups. Examples of suitable carboxylic acids which may be prepared according to the process of this invention would include propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, etc. It is also contemplated within the scope of this invention that the carboxylic acids produced may be either branch-chained or straight-chained compounds. For example, when the unsaturated hydrocarbon comprises 1-tetradecene the resultant carboxylic acid may comprise a pentanoic acid, a methyl-substituted tetradecanoic acid or a dimethyl-substituted tridecanoic acid. The carboxylic acids which comprise the hydroxy alkyl esters would include ethyl butanoate, ethyl pentanoate, propyl hexanoate, ethyl heptanoate, propyl octanoate, butyl nonanoate, ethyl decanoate, ethyl undecanoate, propyl dodecanoate, ethyl tridecanoate, ethyl tetradecanoate, ethyl pentadecanoate, propyl pentadecanoate, 2-hydroxyethyl pentanoate, 3-hydroxypropyl heptanoate, etc. It is understood that the aforementioned carboxylic acids are only representative of the class of compounds which may be employed and that the present invention is not necessarily limited thereto.

The following examples are given to illustrate the process of the present invention which, however, are not intended to limit the generally broad scope of the present invention in strict accordance therewith.

EXAMPLE I

In this example the zeolite-dropping sol blend was prepared by digesting 726 grams of a basic aluminum sulfate slurry (6.89 percent alumina) with 769 grams of an aluminum chloride hydrosol (13.0 percent aluminum; 1.24 aluminum to chlorine ratio) in the presence of 60 grams of mordenite for about 4-5 hours at a temperature of 100° to 105° C. This resulted in 900 cc. of an alumina-chloro-sulfate hydrosol plus mordenite. The sol was cooled and blended with 450 cc. of 28 percent HMT (hexamethylene tetramine) and 50 grams of urea in an aqueous solution amounting to a total of 100 cc. and formed into one-sixteenth inch spheroidal hydrogel spheres which were then transferred to a pressure aging vessel and aged 15 hours at 100° C. The aged spheres were transferred to a wash tower and washed for 3 hours at a temperature of 95° C. with 5 gallons of water containing 20 grams of ammonium nitrate and 20 cc. of aqueous ammonia (28 percent). The washed spheres were removed from said wash tower and dried at 300° F. after which they were calcined for 2 hours at 1,200° F.

Two grams of the above-prepared mordenite are added to a rotating autoclave to which is subsequently charged 19.6 grams (0.1 mol) of 7-tetradecene and 3.6 grams (0.2 mol) of water, said rotating autoclave being equipped with heating and carbon monoxide entry devices. The autoclave is pressed with 100 atmospheres of carbon monoxide and heated to a temperature of 150° C. and maintained thereat for a period of time comprising 2.3 hours. At the end of this period of time, the heating is terminated and the autoclave allowed to return to room temperature. The product is recovered, separated from the catalyst by filtration and analyzed by means of gas-liquid chromatography instrumentation, said analysis disclosing the product to be a mixture of pentadecanoic acids.

EXAMPLE II

In this example, 12.6 grams (0.1 mol) of 2-nonene and 0.36 grams (0.2 mol) of water are added to an autoclave which contains 0.7 grams of a faujasite zeolitic catalyst which has been treated in the alumina hydrosol utilized in Example I and the spheres aged at a temperature of 250° C. for a period of time comprising 10 hours and dried at a temperature of 500° C. and a pressure of 1 atmosphere. The autoclave is equipped with a carbon monoxide entry device and a medium comprising normal -n-pentane. Carbon monoxide is allowed to enter the autoclave to the extent of 15 atmospheres of said carbon monoxide. The autoclave is heated to a temperature of 50° C. and maintained thereat for a period of time comprising 16 hours. At the end of this period of time, the heating is terminated in the autoclave and allowed to return to room temperature. The product is recovered, separated from the catalyst by filtration and analyzed by means of gas-liquid chromatography instrumentation, said analysis disclosing the product to be a mixture of decanoic acids.

EXAMPLE III

In this example, 14.0 grams (0.1 mol) of 5-decene and 18.0 grams (1.0 mol) of water are charged to a 850 ml. glass lined rotating autoclave containing 2.0 grams of the mordenite prepared in Example I. The rotating autoclave is charged with carbon monoxide to a pressure of 50 atmospheres, at which time the autoclave is heated to a temperature of 200° C. The autoclave is maintained at 200° C. for a period of time comprising 3.1 hours, at the end of which the heating is terminated and the autoclave allowed to return to room temperature. The unreacted carbon monoxide is subsequently vented thereby allowing it to return to ambient pressure. The product is recovered, separated from the catalyst by filtration and analyzed by means of gas-liquid chromatography instrumentation, said analysis disclosing the product to be a mixture of undecanoic acids.

EXAMPLE IV

In this example, 8.0 grams (0.1 mol) of 1,4-cyclohexadiene and 1.8 grams (.1 mol) of water are charged to an 850 ml. glass-lined rotating autoclave equipped with heating and carbon monoxide entry devices. The autoclave is pressed with 20 atmospheres of carbon monoxide but the pressure in the rotating autoclave is regulated so as to maintain a constant pressure environment of 20 atmospheres. The autoclave is heated to a temperature of 45° C. and maintained thereat for a period of time comprising 6 hours. At the end of this time, heating is terminated and the autoclave allowed to return to room temperature. The product is recovered, separated from the catalyst by filtration and analyzed by means of gas-liquid chromatography instrumentation, said analysis disclosing the product to be cyclohexenecarboxylic acid and cyclohexanedicarboxylic acid.

EXAMPLE V

In this example, the physical contents of Example I were maintained with the exception that 6.2 grams (0.1 mol) of ethylene glycol are substituted for the molecular quantity of water in Example I. The product is recovered and analyzed in the same procedure as set forth in Example I, said analysis disclosing the product to be 2-hydroxyethyl tetradecanoates and the ethylene glycol bis(tetradecanoates).

Example V is again repeated using butanol-2 and ethyl alcohol in the place of ethylene glycol, the recovered carboxylic acid is a derivative of carboxylic acid respectively, butyl tetradecanoate and ethyl tetradecanoate.

I claim as my invention:

1. A process for the preparation of carboxylic acids and esters thereof which comprises: reacting an unsaturated hydrocarbon from the group consisting of aliphatic olefins and cycloaliphatic olefins with carbon monoxide and a stochiometric excess relative to said unsaturated compound of a compound selected from the group consisting of water, an alkanol possessing from 1 to 10 carbon atoms and an alkandiol possessing from 2 to 10 carbon atoms at a temperature in the range of from about 25° to about 300° C and a pressure of from about atmospheric to about 500 atmospheres in the presence of a catalyst consisting essentially of a crystalline aluminosilicate zeolite which has been treated by dispersing said zeolite in an aluminum hydrosol prior to aging, aging at aging conditions, and drying at drying conditions.

2. The process of claim 1 further characterized in that the zeolitic catalyst is aged at a temperature of about 30° to about 500° C. and a pressure in the range of from 1 to about 100 atmospheres for a period of time from about 1 to about 20 hours.

3. The process of claim 1 further characterized in that the zeolitic catalyst is dried at drying conditions which include a temperature of from about 100° to about 500° C. and a pressure of from about 1 atmosphere to about 100 atmospheres.

4. The process of claim 1 further characterized in that the alumina hydrosol is an aluminum chloride hydrosol.

5. The process of claim 1 further characterized in that the zeolite which is treated is mordenite.

6. The process of claim 1 further characterized in that the zeolite which is treated is faujasite.

7. The process of claim 1 further characterized in that the compound selected from the group consisting of water, an alkanol and an alkandiol is present in a slight stochiometric excess over the quantity of the unsaturated compound.

8. The process of claim 1 further characterized in that the unsaturated compound is 7-tetradecene, the compound selected from the group consisting of water, alkanol and alkandiol is water and the reaction product is pentadecanoic acid.

9. The process of claim 1 further characterized in that the unsaturated compound is 2-nonene, the compound selected from the group consisting of water, alkanol and alkandiol is water and the reaction product is decanoic acid.

10. The process of claim 1 further characterized in that the unsaturated compound is 5-decene, the compound selected from the group consisting of water, alkanol and alkkandiol is water and the reaction product is undecanoic acid.

11. The process of claim 1 further characterized in that the unsaturated compound is 1,4-cyclohexadiene, the compound selected from the group consisting of water, alkanol and alkandiol is water and the reaction product is cyclohexenecarboxylic acid.

12. The process of claim 1 further characterized in that the unsaturated compound is 7-tetradecene, the alkanol is ethanol and the reaction product is ethyl tetradecanoate.

13. The process of claim 1 further characterized in that the alkanol is ethanol.

14. The process of claim 1 further characterized in that the alkandiol is ethylene glycol.

15. The process of claim 1 further characterized in that the alkanol is butanol-2.

* * * * *